(12) United States Patent
Banko (10) Patent No.: US 10,940,039 B2
(45) Date of Patent: Mar. 9, 2021

(54) AUTOMATIC ULTRASONIC PHACOEMULSIFICATION CONTROL

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 447 days.

(21) Appl. No.: 15/799,126

(22) Filed: Oct. 31, 2017

(65) Prior Publication Data
US 2019/0133822 A1    May 9, 2019

(51) Int. Cl.
*A61F 9/007* (2006.01)
*A61M 3/02* (2006.01)
*A61M 1/00* (2006.01)

(52) U.S. Cl.
CPC ....... *A61F 9/00745* (2013.01); *A61M 1/0031* (2013.01); *A61M 1/0058* (2013.01); *A61M 1/0084* (2013.01); *A61M 3/022* (2014.02); *A61M 3/0254* (2013.01); *A61M 3/0258* (2013.01); *A61M 3/0283* (2013.01); *A61M 2205/078* (2013.01); *A61M 2205/3331* (2013.01); *A61M 2205/3334* (2013.01); *A61M 2210/0612* (2013.01)

(58) Field of Classification Search
CPC .......... A61M 2210/0612; A61M 1/003; A61M 1/0058; A61M 1/0064; A61M 1/0031; A61M 3/022; A61M 3/0283; A61M 2205/3331; A61M 2205/3334; A61F 9/00745
See application file for complete search history.

(56) References Cited

U.S. PATENT DOCUMENTS

| | | |
|---|---|---|
| 4,428,748 A | 1/1984 | Peyman et al. |
| 4,504,264 A | 3/1985 | Kelman |
| 5,433,702 A * | 7/1995 | Zelman ............... A61F 9/00745 200/295 |
| 5,591,127 A | 1/1997 | Barwick, Jr. et al. |
| 5,697,898 A | 12/1997 | Devine |

(Continued)

OTHER PUBLICATIONS

International Preliminary Report on Patentability in corresponding PCT Application No. PCT/US2018/055205, dated May 5, 2020.
(Continued)

*Primary Examiner* — Bradley J Osinski
(74) *Attorney, Agent, or Firm* — Leason Ellis LLP (57) ABSTRACT

A phacoemulsification system includes a console connected to a hand piece that has an ultrasonically vibrated cutting tip. The console generates an ultrasonic electrical signal for the cutting tip, provides irrigation fluid and is the source of aspiration force. The console also has a pressure sensor. The control system has automatic operation such that the aspiration force lowers when a first preset pressure limit is reached, and the aspiration force and ultrasonic vibration are turned off at a second preset pressure limit higher than the first. The control system also lowers the aspiration force initially when a change in pressure per unit of time exceeds a preset limit and then increases the aspiration flow if the pressure level drops below the limit.

21 Claims, 7 Drawing Sheets

(56) References Cited

U.S. PATENT DOCUMENTS

| | | | |
|---|---|---|---|
| 5,700,240 A * | 12/1997 | Barwick, Jr. | A61F 9/00745 604/118 |
| 8,277,462 B2 | 10/2012 | Heymann et al. | |
| 2003/0028141 A1 | 2/2003 | Kadziauskas et al. | |
| 2006/0224107 A1 * | 10/2006 | Claus | A61F 9/00745 604/44 |
| 2007/0056596 A1 * | 3/2007 | Fanney | B06B 1/0215 128/898 |
| 2009/0048607 A1 * | 2/2009 | Rockley | A61M 1/0031 606/107 |
| 2009/0118663 A1 * | 5/2009 | Rockley | A61F 9/008 604/20 |
| 2013/0072853 A1 | 3/2013 | Wong et al. | |
| 2014/0114335 A1 | 4/2014 | Banko | |
| 2016/0367735 A1 | 12/2016 | Eddo et al. | |

OTHER PUBLICATIONS

Moyer, "High-vacuum Phaco System Allows Better Intraocular Control," Ophthalmology Times, vol. 19, No. 15, Sep. 15, 1994, 2 pages.

International Search Report and Written Opinion in corresponding PCT Application No. PCT/2018/055205, dated Feb. 5, 2019.

\* cited by examiner

| | ULTRASOUND (U.S.) | | | | | | FLOW (cc/min) | | |
|---|---|---|---|---|---|---|---|---|---|
| | ON/OFF | LINEAR POWER (Change U.S. power up or down) | VARIABLE POWER (Change up or down) | Pulse U.S. Power ON/OFF | Pulse U.S. Power ON/OFF | Pulse U.S. Power ON/OFF | | | |
| Vacuum (mm/Hg) Change over time = Rate | | Graph of U.S. power amplitude is a straight line | Graph of U.S. power amplitude is a curved line | Fixed time between fixed U.S. power amplitude | Variable time between fixed U.S. power amplitude | Variable time between pulses and variable U.S. power amplitude. Both linear and curved U.S. power amplitude | Reduced flow based on rate of vacuum change | Flow reduction in several steps. For example: Maximum flow is set at 50cc/min and maximum vacuum limit is set at 500 mmHg. When a pre-set vacuum threshold of 200mmHg is reached, the flow is reduced first to 6cc/min, and then after 5 seconds can reduce to 2cc/min | Reduced flow can be in several steps, and each step can have a curved, nonlinear decrease. |
| | C1 | C2 | C3 | C4 | C5 | C6 | D1 | D2 | D3 |

AUTOMATIC ULTRASONIC PHACOEMULSIFICATION CONTROL

TECHNICAL FIELD

The present invention is generally directed to apparatus for controlling the movement of fluids and ultrasonic vibration during phacoemulsification surgery and, more particularly, for automated control.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

U.S. Pat. No. 4,504,264 of Kelman depicts an ultrasonic hand piece that includes a transducer means for generating mechanical vibrations upon excitation with an alternating-current electrical signal. The transducer is coupled to a work tip by means of a connecting body that forms an acoustic impedance transformer for conveying the longitudinal vibrations of the transducer into the work tip. The work tip is an elongated hollow tube of a suitable metal, such as titanium, that is capable of supporting ultrasonic vibrations. It has a distal end of a desired shape that is placed against the tissue that is emulsified by the mechanical vibration of the tube. The distal end of the work tip tube is surrounded by a sleeve 17, which forms a channel through which irrigation fluid is directed to the surgical site. The emulsified tissue and fluid are aspirated through the tube by a suction force.

Thus, for the hand piece to operate it must be provided with an electrical signal to drive the ultrasonic vibrations. In addition, it must be provided with irrigation fluid and it must withdraw aspiration fluid. These are provided by a control apparatus such as that disclosed in U.S. Pat. No. 5,697,898 of Devine. The Devine patent discloses a phacoemulsification machine console connected to a hand piece. The machine supplies irrigation or infusion fluid from an infusion reservoir to the hand piece through an infusion tube. It also removes emulsified tissue through the hand piece and an evacuation tube connected to a vacuum pump. The pump deposits the tissue in a container. It also provides an electrical signal to the hand piece to drive the ultrasonic vibration transducer.

The Devine patent points out that it is important that the intraocular pressure remains nearly constant. Where a vacuum pump is used to draw fluid from the eye, a constant pressure is achieved by keeping the rate of fluid flow from the eye equal to the fluid being drawn into the eye from the infusion reservoir. However, if the evacuation port becomes occluded by, for example, cataract material, a pressure differential is created with positive pressure occurring inside the eye because of infusion and negative pressure (vacuum) occurring inside the handpiece and/or evacuation line. Unless relieved, this pressure differential will increase as the pump continues to generate a vacuum. When the occluding material is eventually sucked into the evacuation tube, the sudden rush of fluid and/or sucking forces may cause the above-identified damage to the eye. For example, the sucking force can produce unpredictable penetration of the epinucleus and concomitant rupture of the lens capsule. This could then create vitreous loss and its associated risks, including retinal detachment and Cystoid Macular Edema ("CME"). Vitreous loss is associated with increased risks including retinal detachment and, therefore, is undesirable.

As indicated in the Devine patent, well defined pressure limits can be set such that when they are exceed, the pump is turned off to prevent further damage. Also, an evacuation line can be opened through a vent valve to reduce the pressure in the aspiration tube. Typically the vacuum limit may be set directly on the machine console.

The invention in the Devine patent utilizes an "automated free flow mechanism" ("AFF") which has a free flow valve designed to allow the free flow of fluid from the infusion reservoir into the eye, through the evacuation port of the handpiece and the evacuation tubing, and into a collection container. The AFF utilizes the positive pressure created by placing the infusion bottle at a higher position relative to the evacuation line, to create a flow of material from within the eye through the evacuation port of the handpiece, without the use of a pump. Although no vacuum pressure is required to cause this fluid flow out of the eye, vacuum pumps may still be used where the surgeon requires accelerated removal of cataract material once the material is maneuvered safely away from the delicate lens capsule within the eye. In such a situation, the free flow valve provides enhanced surge protection, i.e., protection from the sudden rush of fluid and/or sucking forces when a piece of tissue blocking the evacuation line is suddenly removed.

When the surgeon selects the AFF mode on the phacoemulsification machine console the computer logic of the machine automatically shuts down the vacuum pump and permits the surgeon to open the free flow valve with a surgeon-controlled foot pedal. Also, the machine may be configured so that the vent valve is opened automatically whenever the surgeon places the foot switch in a particular position.

The ultrasonic power may be predetermined in terms of percentage of stroke amplitude (power) and in terms of pulse modality. For example, 30 percent power with a pulsed ultrasonic power mode set to a rate of 6 (6 cycles per minute) could be programmed as a specific console setting or control button with a specific label indicating its use for free flow removal of the epinuclear shell. Another option would be to allow the surgeon to select these parameters (power, pulse) independently.

In a manual entitled "The Ocusystem$^{ART}$," Surgical Design Corporation dated Dec. 29, 2010, the operation of a more modern system is described. The Ocusystem is a sleek, low profile console with easy to reach and easy to use control knobs located up-front on the main control panel. The unit also provides an LED digital display, a series of push buttons that light when activated and an audible warning sound that can be controlled with a dial. Attached to the system are a hand piece driven by an ultrasonic electrical signal from the console, an irrigation fluid supply for delivery of irrigation fluid to the hand piece, an aspiration line that accepts tissue from the hand piece. A foot switch in the form of a foot pedal is provided to control operation. Depressing the foot pedal activates various positions. For example, position "0" is the ready position, position "1" begins infusion, position "2" activates aspiration and position "3" turns on the ultrasound. Continuing to depress the footswitch in position "3" will activate linear control of the phacoemulsification power.

This system not only supplies the ultrasonic signal in a continuous mode, it also provides pulsed mode ultrasound. In addition this system has transducers that sense and react to sudden changes in intraocular pressure. Further, it provides an Adjustable Rise Time (ART) control that permits the surgeon to choose the specific point in the vacuum cycle at which the aspiration flow rate can be changed or altered on an automatic basis (faster or slower) to provide greater control and safety during the phacoemulsification ("phaco") surgical procedure. In particular, "ART" allows the surgeon to set the machine for a higher pump speed or flow rate [cc/min], and at a preselected vacuum occlusion setting [mm Hg], "ART" then automatically slows down the pump speed to a secondary or slower flow rate. The advantage is that it gives the surgeon better control while molding the nuclear material during phaco. See also, Moyer, "High-vacuum Phaco System Allows Better Intraocular Control," *Ophthalmology Times*, Vol. 19, No. 15 (1994). In addition the system incorporates a system to prevent a sudden increase in vacuum when a piece of nuclear material is suddenly aspirated into the tip. This system is like that in the Devine patent.

With respect to the ultrasonic vibrations the phaco procedure can be considered in at least two phases. In the beginning the ultrasonic vibration is turned on, e.g., by placing a foot pedal in position 3. During this phase the cataract can be split up or broken into small pieces. At this point the surgeon can stop the vibration by lifting his or her foot from the pedal. However, the aspiration force remains on. The surgeon uses this aspiration force to collect the smaller pieces of tissue and to deliver them to the container through the hand piece. Should one of the pieces be too large, it can block or occlude the aspiration tube, which will cause the aspiration pressure to build. In order to clear this tissue, the surgeon using the foot pedal turns on the ultrasonic vibration again. The difficulty is that the surgeon may not respond quickly and the pressure can build to a dangerous level.

The prior art phaco systems had some safety limitations that would automatically change the operation to prevent injury to the patient when an unsafe condition is reached, e.g., high pressure due to an aspiration line clogged with tissue. These are typically vacuum pressure limits that regulated fluid flow, particularly aspiration suction force, in the face of excess vacuum pressure. However, once the system has hit a vacuum limit, damage may already have been done. Thus, it would be beneficial if the phaco system could anticipate a condition before a limit is reached and automatically take steps to address it.

SUMMARY OF THE INVENTION

In accordance with the invention the operation of a phaco system is automatically controlled to avoid unsafe conditions.

In one illustrative embodiment the phacoemulsification system includes a hand piece with a cutting tip, e.g., a phaco tube or knife extending from a distal end of the hand piece. An ultrasonic transducer is connected to the cutting tip and mechanically vibrates it at an ultrasonic frequency when an ultrasonic electrical signal is applied to the transducer. Both at least one irrigation channel for providing irrigation fluid near the distal end of the cutting tip, and at least one aspiration channel for collecting fluid and tissue near the distal end of the cutting tip are included.

The system includes a console with an electrical signal generator for generating the ultrasonic electrical signal and providing it to the transducer of the hand piece. The system also includes an irrigation supply for providing irrigation fluid through an irrigation tube to the irrigation channel of the hand piece. A source of aspiration force for extracting aspirated fluid and tissue through an aspiration tube from the aspiration channel of the hand piece is typically implemented with a pump that is contained within the console or is at least controlled by the console. Further the phacoemulsification system includes a control system within the console for determining the irrigation flow rate, the aspiration flow rate and the amplitude of the ultrasonic electrical signal. Finally, a pressure sensor is provided in the aspiration channel for measuring the pressure over a period of time.

As was known from the prior art, when the sensor detects a first preset pressure limit in the aspiration tube, the control system automatically causes the source of aspiration force (e.g., the aspiration pump) to lower the rate of aspiration. When the sensor detects a second maximum preset pressure limit higher than the first, the control system automatically causes the source of aspiration force to turn off.

However, the control system of the present invention also automatically operates on the basis of the rate of change of pressure in the aspiration tube. In particular, when the sensor detects a change in pressure per unit of time that exceeds a preset limit for the rate of change, the control system also causes the source of aspiration force to lower the rate of aspiration. Thus, even before the pressure limit is reached, if the pressure is rising too quickly, the system takes action such as lowering the speed of the aspiration pump so as to slow the rate of rise of the pressure. At this point the system can check to see if the rate has dropped below a preset limit. If it has the aspiration pump speed can be increased again. The control system can also be set to shut down the aspiration pump and the ultrasonic vibrations if the rate is too high.

The present invention is further distinguished from the prior art in that the control system of the phacoemulsification system also automatically affects the ultrasonic vibrations based on the level of pressure in the aspiration tube. In particular, during the first phase of a phaco operation when the surgeon has his or her foot on the pedal to cause vibration. When the sensor detects a preset pressure limit the control system causes a first drop in the amplitude of the ultrasonic electrical signal to a point where there is no longer mechanical vibration of the cutting tip. This first drop can occur over a period of time. Also, during the second phase of a phaco process when the surgeon has stopped the vibrations and is merely sucking in tissue pieces, if a piece blocks the aspiration tube and the sensor detects a pressure beyond a preset limit, the control system automatically turns on the vibrations to break up the piece of tissue.

When the sensor detects a change in pressure per unit of time (rate of change) that exceeds a preset limit, the control system causes a second drop in the amplitude of the ultrasonic electrical signal to a point where there is no longer mechanical vibration of the knife. The second drop may also be over a period of time, and the first drop (based on pressure level) and the second drop (based on rate of change) are independent of each other.

In addition to the pressure limit and the rate of change of pressure, the present invention may also include an additional or third variable to control both the ultrasound and flow. This third variable is the ratio of the rate of vacuum change to the current vacuum limit. Thus, automatic control can be based on how fast the pressure is approaching the limit. Stated another way, the period of time in which the pressure will reach the limit can be a controlling factor. For example, if the rate of change is 5 mmHg per second and the vacuum limit is 200 mmHg, then the ratio is 200 divided by 5, i.e., a period of 40 seconds. With 40 seconds until the limit is reached, the system can be programmed to merely slow the rate of aspiration. If the period was 10 seconds, more drastic action might be programmed, e.g., stopping the pump and the vibrations at once.

It should be noted that the system is generally mechanical with pumps, tubes and flowing fluids. As a result, there is inertia so nothing happens immediately. If there is a rapid pressure rise, there is the possibility the pressure will significantly overshoot the limit before the pump or vibrations are fully stopped. By using the rate of change as a parameter, it is possible to intervene in such a case and stop the system before the vacuum limit is even reached.

In addition to these three variables controlling the ultrasound and aspiration flow, they may also be used to control pressurized irrigation or, if the irrigation is not pressurized, then the height of the IV pole that contains the irrigation bottle. The height of the bottle will determine the irrigation pressure.

The automatic operation of the present invention, in addition to controlling the aspiration pump (and perhaps the irrigation pump) as well as the ultrasonic vibration, can also control valves that determine the flow of fluid through the hand piece. In particular, the operating end of the work tip may be designed with a cutting knife or hollow phaco tube and multiple fluid channels. The three variables can control which channels are used for irrigation and which are used for evacuation (aspiration). For example, if the rate of vacuum rise is too high then one of the aspiration tubes can be converted to an irrigation tube to slow down the vacuum rise.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 1:
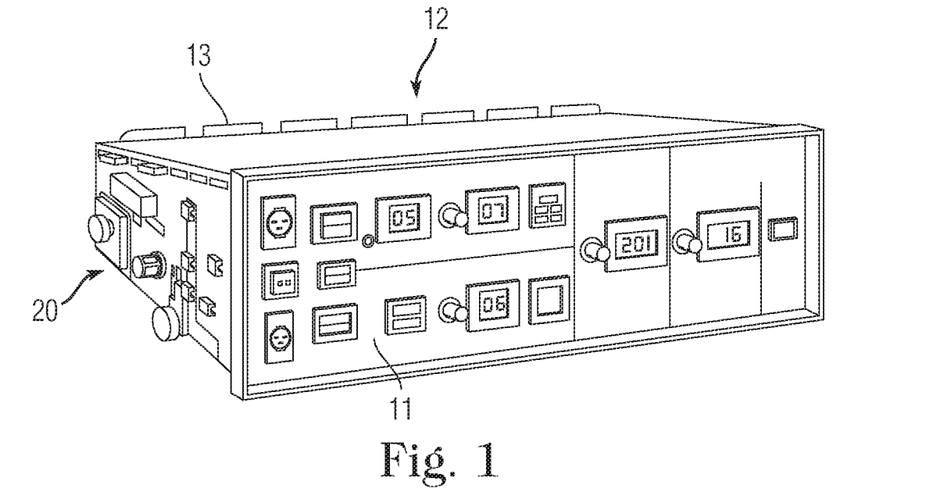
FIG. 1 is a view a perspective view of a console for a phacoemulsification system that can be utilized in practicing the present invention.

FIG. 1 illustrates a console 12 of a phacoemulsification system 10 used for cataract surgery on either humans or animals. The console has a control panel 11 and a housing 13 behind the control panel. Various controls are shown on the control panel and additional controls can be located on a back panel (not shown). The left side panel of the console has a pump apparatus 20 and fasteners for various tubes as shown more clearly in FIG. 2.

Figure 2:
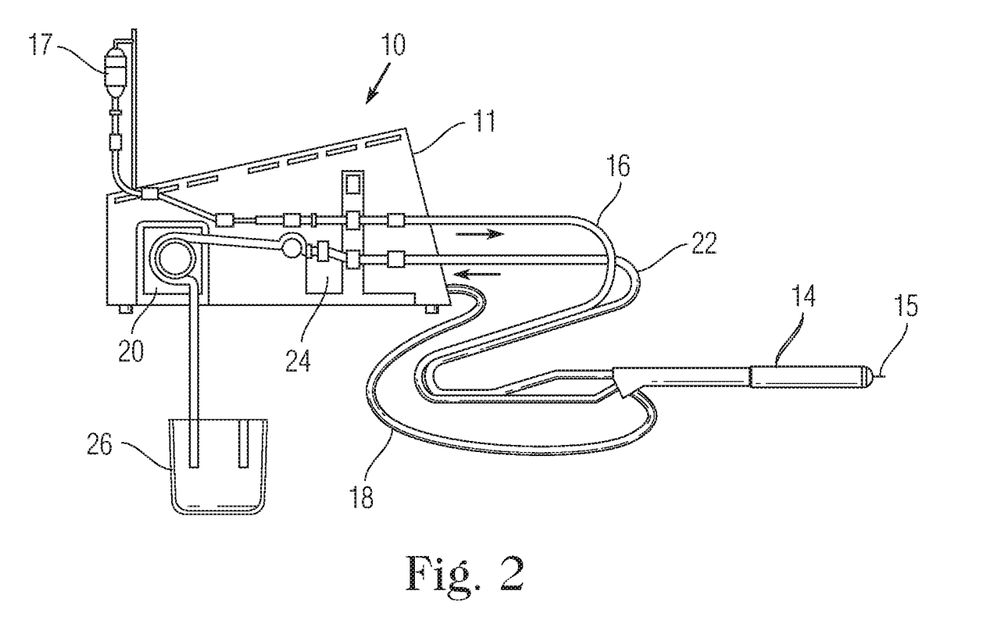
FIG. 2 is a side view of the console of FIG. 1 showing other elements of the phacoemulsification system of the present invention.

In addition to the console, FIG. 2 shows the other elements of the phacoemulsification system 10. These include an irrigation reservoir 17 containing irrigation fluid (e.g., saline solution). It is connected to a surgical handpiece 14 by irrigation line 16. The surgical hand piece has a work tip 15. The vacuum pump 20 is connected to the surgical handpiece 14 by an aspiration line 22. The vacuum pump 20 may be activated to provide suction for removing fluid and cataract particles from the eye during surgery.

An ultrasonic electrical signal is provided to hand piece 14 by means of a cable 18. This signal drives a transducer within the hand piece 14, which results in ultrasonic mechanical vibration of the work tip 15. During phaco surgery this vibration acts to breakup and emulsify cataract tissue. Irrigation fluid from reservoir 17 is delivered by tube 16 to hand piece 14. It passes through hand piece 14 and is bathed onto the surgical site during this process. The cataract tissue and surrounding fluid are aspirated through the work tip 15 and hand piece 14 by a suction force created by pump 20 in tube 22. After passing through pump 20 the tissue and fluid are deposited in container 26.

After the phaco portion of cataract surgery, the posterior lens of the eye capsule must be cleansed of cataract fiber and plaque in order to provide a successful visual outcome. This is done by either mechanically scraping the lens capsule with curettes and various sand blasted cannulas, or by vacuuming the lens capsule with an irrigation/aspiration (I/A) hand piece. This latter approach uses the vacuum pump 20 to create low levels of vacuum pressure which, in turn, cause fluid to flow from the irrigation reservoir 17 through the inside of the eye, and into an aspiration port located at the tip of the I/A hand piece. The I/A hand piece tip is maneuvered over the posterior lens capsule, thereby vacuuming the lens capsule. If the lens capsule is too flaccid, or if too much vacuum is created, the lens capsule can be aspirated into the hand piece aspiration port, thereby occluding the aspiration port. When this occurs, a pressure differential is created across the aspirated lens capsule, with a positive pressure outside the tip (within the eye) and a negative pressure or vacuum inside the tip. Unless relieved, this pressure differential will increase as the vacuum pump 20 continues to generate the vacuum. This could eventually cause the lens capsule to tear, resulting in the disruption of the vitreous or "vitreous loss" and its attendant undesirable outcomes.

Figure 3:
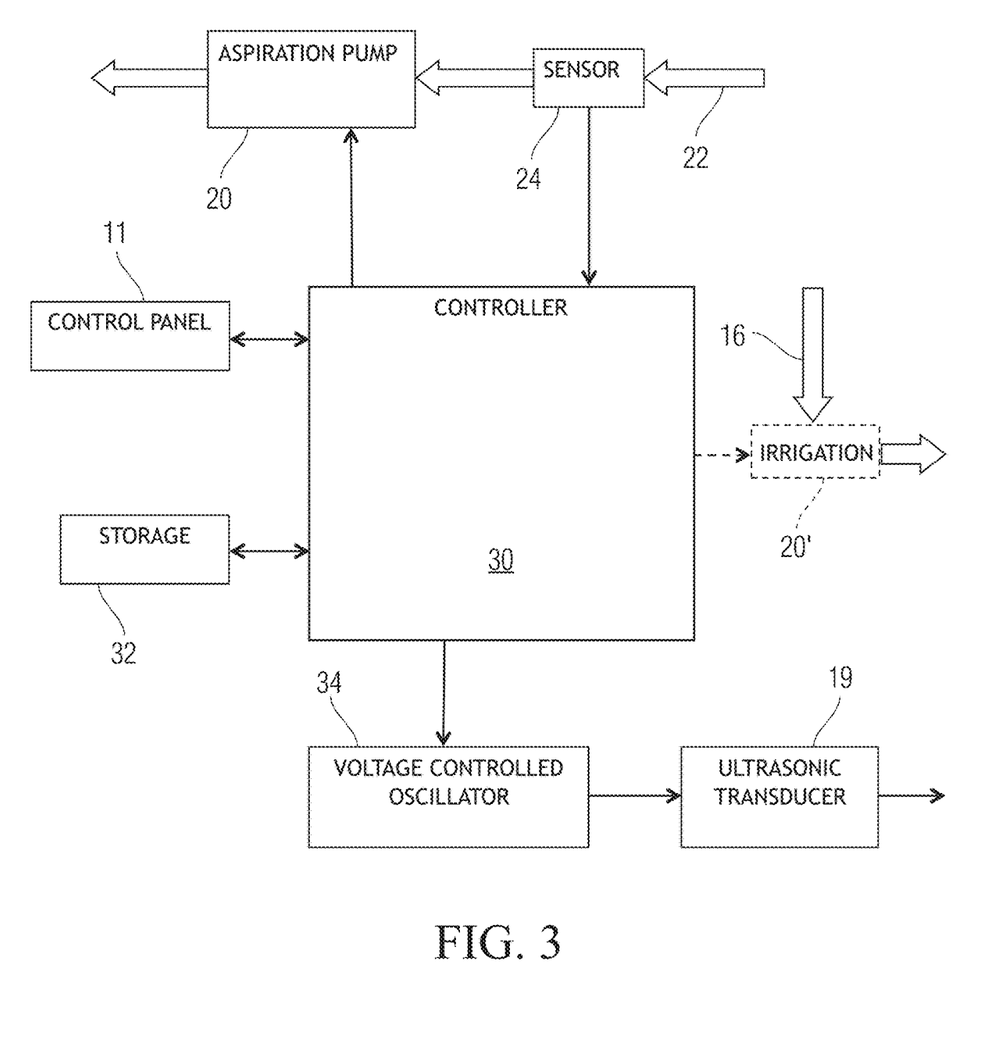
FIG. 3 is a schematic diagram of an exemplary embodiment of a control system of the present invention.
Figure 4A:
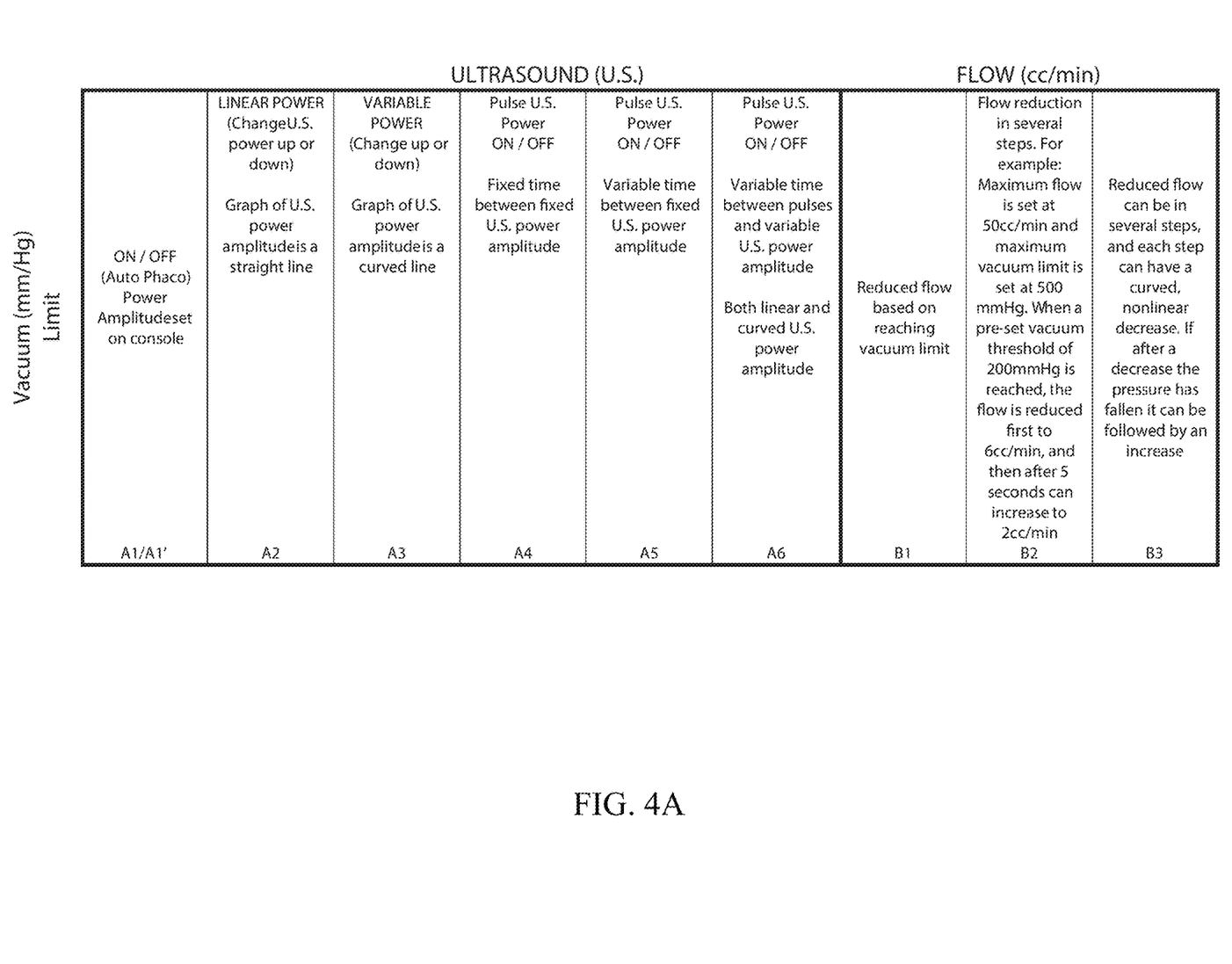
FIG. 4A is a chart of the various operational modes of the phacoemulsification system of the present invention based on the rate of change of the aspiration pressure and FIG. 4B is a similar chart based on the level of aspiration pressure.
Figure 4B:
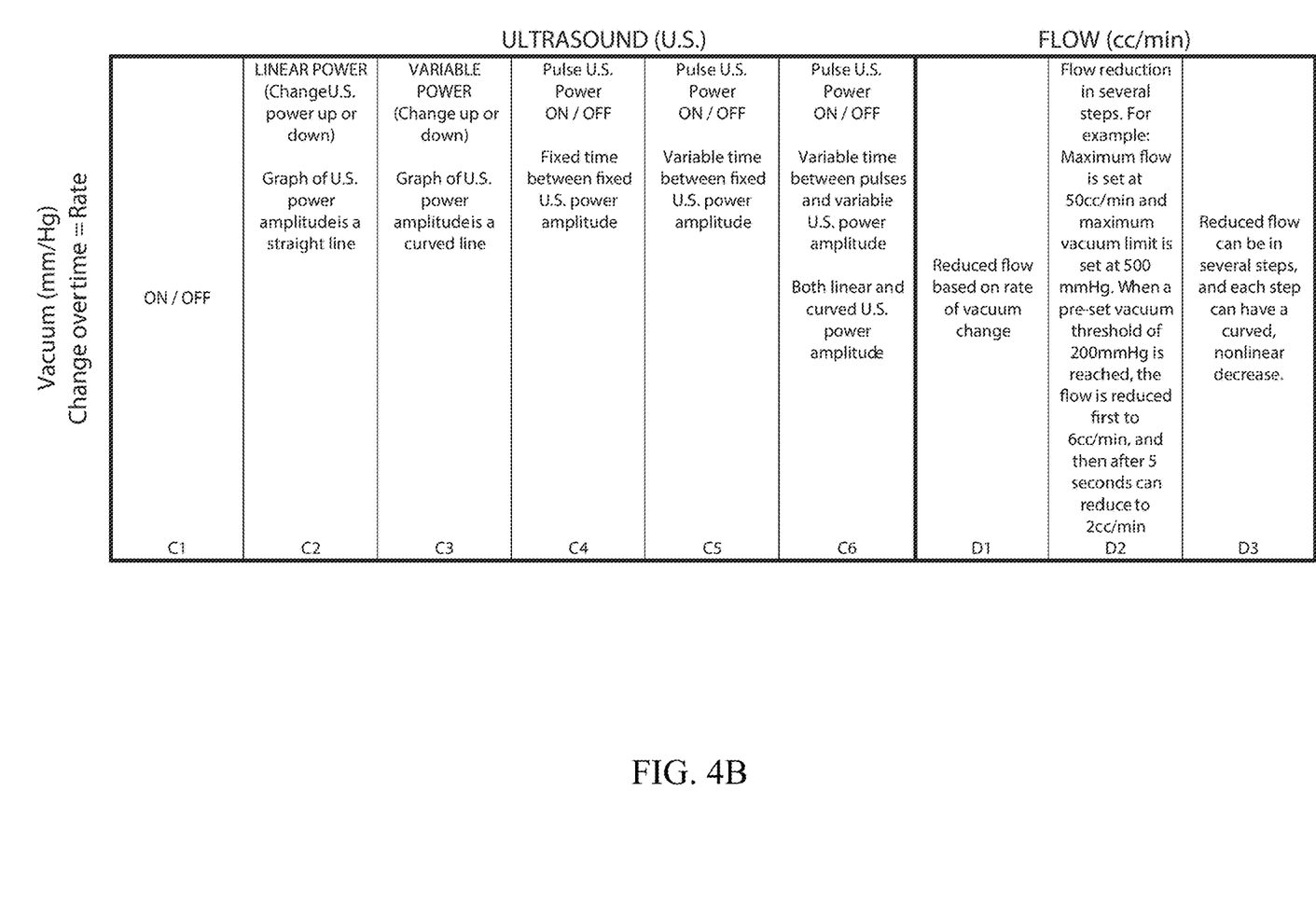
Figure 5:
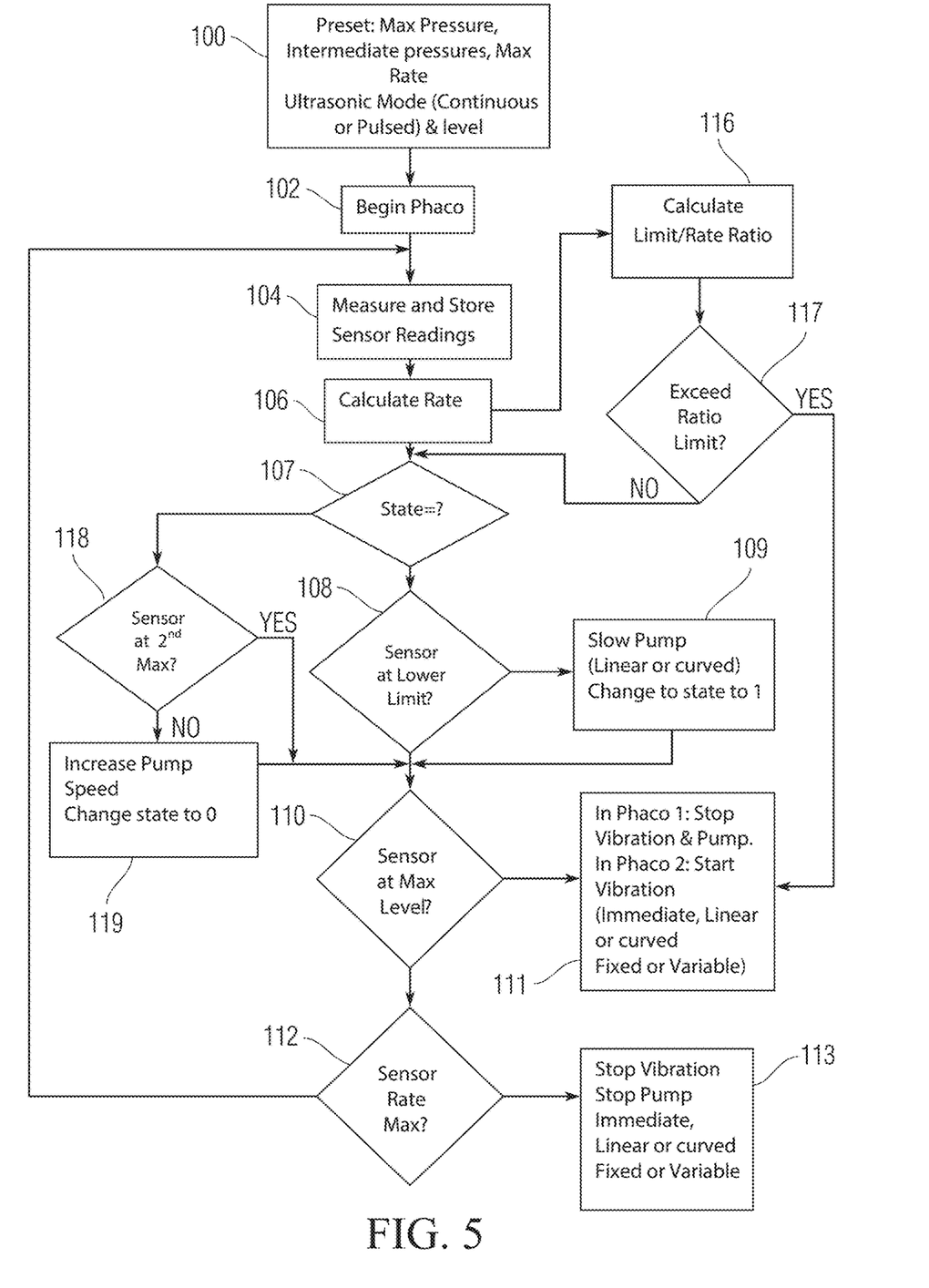
FIG. 5 is a flow chart showing the operation of the control system of the present invention so as to provide the various operational modes of the phacoemulsification system of the present invention.

In order to avoid this condition a pressure sensor 24 is provided in the aspiration line 22. When the pressure in line 22 exceeds a preset limit, which may be entered by the user on control panel 11 or the controls on the rear panel, the control circuit of the system automatically causes the pump 20 to stop. A schematic of the control circuit is shown in FIG. 3 and a flow chart of its operations is shown in FIG. 5. FIGS. 4A and 4B are charts showing various automatic operational modes of the phacoemulsification system of the present invention that are used to avoid undesirable conditions.

The schematic of FIG. 3 shows a controller 30, which may be a programmed computer, programmed gate array, set of analog operational amplifiers, a logic circuit or mechanical relays. To the extent controller 30 is a computer, it is provided with storage 32, which can store its operating program as well as data. Information for use by controller 30 can be input by the user through control panel 11. The controller 30 is designed to produce signals that control the aspiration pump 20 based on the aspiration pressure in aspiration line 22 as determined by pressure sensor 24. The controller 30 also controls an oscillator 34 that generates the ultrasonic signals that drive the transducer 19 in the hand piece 14. (FIG. 6) This signal causes the mechanical vibration of work tip 15 that emulsifies the tissue.

In a common operation as shown in FIG. 2, saline solution from irrigation reservoir 17 passes though tube 16 and the hand piece to the operation site by means of gravity. However, it is also possible to include an irrigation pump in line 16 so as to have forced irrigation.

Some of the various modes in which the phacoemulsification system can operate to automatically provide protection against conditions that can harm the eye of the patient are listed in FIGS. 4A and 4B.

The charts have 4 categories of operation as follows:

A. Turning the mechanical ultrasonic vibration (pulsed, linear, nonlinear) on or off based on the vacuum level in the aspiration line reaching a preset maximum (6 modes), where turn on occurs when the system is in phaco phase 2, and the turn off occurs when the system is in phaco phase 1;

B. Reducing the flow of aspirated tissue and liquid based on the vacuum level in the aspiration line reaching a preset limit lower than a maximum limit, decreasing the flow again at a second or third limit below the maximum; and increasing the flow rate once it has been reduced if the pressure is below one of the preset limits. (3 modes);

C. Turning the mechanical ultrasonic vibration (pulsed, linear, nonlinear) on or off based on the rate of change of the vacuum level in the aspiration line reaching a preset maximum (6 modes), where turn on occurs when the system is in phaco phase 2, and the turn off occurs when the system is in phaco phase 1; and D. Reducing the flow of aspirated tissue and liquid based on the rate of change of the vacuum level in the aspiration line reaching a preset maximum (3 modes). If the rate of change limit is provided below the maximum, increasing the flow rate once it has been reduced if the pressure is below one of the preset limits, The first modes in categories A and B (A1' and B1 in FIG. 4A) represent the prior art. With particular reference to mode A1, if the sensor 24 detects a pressure in line 22 that exceeds the maximum preset level, the controller either turns off the ultrasonic vibration [Mode A1] or turns it on [Mode A1'], depending on the phase of phacoemulsification. This is represented by steps 110 and 111 in the flow chart of FIG. 5. In particular, during the first phase of the phaco process when the vibrations are generated because the surgeon is operating the foot pedal, should the pressure sensor reach a maximum preset level; the control system will stop the vibrations. [Mode A1] During the second phase of the phaco process when the vibrations are no longer being used and the surgeon is collecting tissue pieces using the aspiration force, should the pressure sensor reach the maximum level (indicating a clogged aspiration tube) the control system turns on the vibrations to break up the clog, which is part of the prior art Ocusystem$^{ART}$ system [Mode A1'].

With regard to mode B1, if the sensor detects a first lower limit in line 22, it reduces the aspiration flow rate by slowing down pump 20. This is represented by steps 108 and 109 in the flow chart of FIG. 5, where the maximum (step 110) is the highest sensor limit, and the lower limit (step 108) is the lower sensor level at which the aspiration pump 24 is caused to slow. In addition to this single breakpoint at which the rate of flow changes, other break points can also be programmed into the system. Thus, as the pressure in the aspiration tube reaches higher and higher limits, the flow is reduced more at each limit.

In Modes A2 and A3 in FIG. 4A, the ultrasonic power may be continuous, linear in the form of a linear saw tooth signal or curved in the form a curved saw tooth signal. In these modes the ultrasonic signal is not simply turned on or off as in Mode A1. Instead, it is increased or decreased over a short period of time. In Mode A2 the increase/decrease is linear. In Mode A3 the increase/decrease is non-linear and can be represented by a curved line. This is represented by steps 110 and 111 in the flow chart of FIG. 5, where Step 111 calls one of (a) stopping the vibration immediately, (b) stopping it in a linear fashion over a short period of time or (c) stopping it in a non-linear or curved fashion over a short period of time.

While the ultrasonic vibration is typically uniform, it can also be applied in pulses. This is one of the parameters selected by the user before operating the system by means of inputs provided from the control panel 11. See Step 100 of FIG. 5. In Mode A4, which utilizes pulsed ultrasonic power, the decrease in the vibrations occurs at a fixed time between pulses. In Mode A5 the decrease in the vibrations occurs at a variable time between pulses. This is illustrated by step 111 in FIG. 5 which provides for stopping the vibration at either fixed times after the pulse or variable times.

In the A6 Mode of operation the ultrasonic vibration is in the form of pulses that occur at variable times. In this mode, when the maximum pressure limit is reached (Step 110), the decrease or start of ultrasonic vibrations occurs at a variable time between the variable pulses. In this mode the decrease can be immediate, linear over a short period of time or curved over a short period of time as indicated by Step 111 in FIG. 5.

In category B the flow of the aspiration pump is controlled based on a lower or interim pressure maximum. As noted above, when a lower limit is reached the aspiration pump 20 has its flow reduced in Mode B1. In Mode B2 the flow is reduced in several steps and each step can be a linear or non-linear decrease in flow. For example when the vacuum level reaches a specific value, the flow can first be 6 cc/min, and after 5 seconds it can jump directly to 2 cc/min. For Mode B3, the flow is reduced in several steps where each step can have a curved or nonlinear decrease. These are all encompassed in Steps 108 and 109 of FIG. 5.

It should be noted that in step 109 a flag is set to indicate a change in the state of the control system from state=0 to state=1. This is an indication that the lower limit level (e.g., 200 mmHg) has been exceeded. If the result of the slowing of the pump is to cause the aspiration pressure to drop below the lower limit level, the system will automatically increase the flow rate. In particular, after step 109, the system checks in step 110 to see if the maximum level (e.g., 300 mmHg) has been exceeded. If not, the system checks in step 112 to see if the maximum rate of change in pressure has been exceeded. If not the system recycles through steps 104 and 106. However, in step 107 the state of the system is checked. If it is in state 0 the lower level is again checked in step 108. However, if as a result of a previous reduction in flow in step 109, the state is 1, the lower limit level is checked in step 118. If at that point the pressure is below the lower limit, the pump speed is increased in step 119 and the state is changed back to 0. If the pressure is above the lower limit, the system returns to step 110 without any increase in flow. Thus in Mode B3 the flow can first be decreased. If this causes the pressure to decrease, the flow can later be automatically increased.

In category C shown in FIG. 4B the rate of change of pressure is used to control the ultrasonic vibrations. Returning to FIG. 3, the controller 30 reads the pressure in line 22 as detected by sensor 24. This is typically done periodically over time. This data is stored in storage 32. Using this data the controller calculates the rate of change of the pressure. This calculation is indicated as Step 106 of FIG. 5. Prior to a phaco operation, a preset value for the maximum rate of change is stored in storage 32 by inputs from control panel 11. See Step 100 of FIG. 5.

According to Mode C1, if the rate limit is exceeded the ultrasonic vibrations are turned on or off depending on the phase of the phaco operation. This is indicated by steps 112 and 113 in the flow chart of FIG. 5. In particular during phase 1 the surgeon wants the vibrations to be on in order to break up the cataract. However, if there is an unacceptable rate of rise in the pressure, the control will turn off the vibrations. Likewise, if the surgeon wants the vibrations off while sucking up pieces of tissue during phase 2 of the phaco operation, the control system will automatically turn on the vibrations if a piece of tissue gets stuck in the aspiration tube and causes the pressure to rise.

The idea here is that if the rate of change is very high, an unsafe condition will be reached quickly. Rather than wait for the maximum pressure to be reached, the vibration is quickly terminated or started before damage can be done. In Modes C2 and C3 as in Modes A2 and A3, the ultrasonic power is not simply turned off immediately as in Mode C1. Instead, it is decreased over a short period of time. In Mode C2 the decrease is linear. In Mode C3 the decrease is non-linear and can be represented by a curved line. This is represented by steps 112 and 113 in the flow chart of FIG. 5, where Step 113 calls for one of (a) immediate stopping of the vibration, (b) decreasing it in a linear fashion or (c) decreasing it in a non-linear or curved fashion.

As with Modes A4-A6, Modes C4-C6 relate to the state where the system is using pulsed ultrasonic vibrations. In Mode C4, which utilizes pulsed ultrasonic power, the decreasing of the vibrations occurs at a fixed time between pulses. In Mode C5 the decreasing of the vibrations occurs at a variable time between pulses. This is illustrated by step 113 in FIG. 5 which provides for stopping the vibrations at either fixed times after the pulse or variable times.

In the C6 Mode of operation the ultrasonic vibration is in the form of pulses that occur at variable times. In this mode, when the maximum rate limit is reached (Step 112), the decrease of ultrasonic vibration occurs at a variable time between the variable pulses. In this mode the decrease can be immediate, linear over time or curved over time as indicated by Step 113 in FIG. 5. It should be noted that the automatic turn on of vibrations, e.g., when in the second phase of a phaco operation and occlusion occurs, the turn on is immediate.

In Modes C1 to C6, when the system is in the phaco 2 phase with the surgeon not pressing on the foot pedal and the vibrations stopped, if there is a rise in pressure that exceeds a limit, the vibrations are restarted to break up the occlusion causing the pressure rise. In Modes C2 and C3 the vibration is turned on linearly or according to a curve, so there is not an immediate jump in mechanical vibration. In modes C4 to C6, which use pulsed vibrations, they are turned on between pulses, either at a fixed time between fixed pulses, a variable time between fixed pulses or a variable time between variable pulses.

Category D also involves automatic control based on the rate of change of the pressure in line 22. However, in this category, control is with respect to the aspiration pump 20. Mode D1 involves a reduction in the flow rate when the rate of change of pressure exceeds a lower level. This is presented by Steps 112 and 113 in FIG. 5. In this D1 Mode the switch to reduced flow is immediate.

Referring to FIG. 5, if no limit has been reached by Step 112, the process circulates back to step 104 and continues.

Like Mode B2, in Mode D2 the flow is reduced in several steps. For example when the vacuum rate reaches a specific value, the flow can first be 5 cc/min, and after 5 seconds it can jump directly to 2 cc/min. For Mode B3, the flow is reduced in several steps where each step can have a curved or nonlinear decrease. These are all encompassed in Step 113 of FIG. 5. Note that unlike Mode B3, once the maximum rate of change has been exceeded, the system does not automatically try to increase the flow rate again. This is because in Mode B3 the pressure level could be checked to be sure it was still safe to increase the flow and hence the pressure. In this mode D3 only the rate is used to control operation and an increase could occur when the system is near the maximum.

It should be noted that the system is generally mechanical with pumps, tubes and flowing fluids. As a result, there is inertia so nothing happens immediately. If there is a rapid pressure rise, there is the possibility the pressure will significantly overshoot the limit before the pump is fully stopped. By using the rate of change as a parameter, it is possible to intervene in such a case and stop the system before the limit is even reached.

The charts of FIGS. 4A and 4B describe controlling ultrasonic vibrations and aspiration fluid flow based on two variables: 1) Rate of Vacuum increase or decrease and 2) Reaching the vacuum limit. A ratio of these variables can also represent a third control parameter. This third variable is the ratio of the rate of vacuum change to the current vacuum limit. Thus, automatic control can be based on how fast the pressure is approaching the limit. Stated another way, the period of time in which the pressure will reach the limit can be a controlling factor. For example, if the rate of change is 5 mmHg per second and the vacuum limit is 200 mmHg, then the ratio is 200 divided by 5, i.e., a period of 40 seconds. With 40 seconds until the limit is reached, the system can be programmed to merely slow the rate of aspiration. If the period was 10 seconds, more drastic action might be programmed, e.g., stopping the pump and the vibrations at once.

Thus, there can be a further mode E, which is not shown in the chart of FIGS. 4A and 4B. This mode relies on both the maximum preset pressure level and the measure of the rate of change of the vacuum in the aspiration line. Basically the ratio of category E is a determination of the time it will take to reach the maximum level given the measured rate of change of pressure. When the ratio exceeds a preset limit, the pump and vibrations are turned off. If it reaches a lower limit the flow may be slowed, and if the system is in phaco phase 2 with the vibration off, the vibrations may be turned on again.

As shown in FIG. 5, after the rate is calculated in Step 106 the value is passed to step 116 which calculates the limit/rate ratio. This ratio is checked in Step 117. If it is larger than a preset value, the control stops the vibration and fluid flow in Step 111 as if the system were being used in the first phaco stage. Otherwise the process continues at Step 108.

The third variable of Mode E, instead of being a ratio, may be some other combination of parameters. For example, instead of dividing the vacuum limit by the rate of change, a new parameter may be obtained by multiplying the two numbers or adding them.

In addition to these three variables controlling the ultrasound and aspiration flow, they may also be used to control pressurized irrigation. As shown in FIG. 3 an irrigation pump 20' may be used to provide pressure for the delivery of irrigation fluid. Since it is helpful with respect to pressure in the eye to have the irrigation and aspiration fluid flows balanced, in the case where there is an irrigation pump it should be controlled in the same way as the aspiration pump described above. If the irrigation is not pressurized by a pump and relies on gravity flow, then the irrigation reservoir 17 shown in FIG. 2 can be located on a motorized pole. The control system then controls the height of the reservoir above the eye, which will determine the irrigation pressure and balance it with the aspiration.

As noted above, ratio check 117 could be two or more checks of the ratio at a maximum level and at one or more lower limits. In such a case, if the system reaches one of the lower limits the flow may be slowed, and if the system is in phaco phase 2 with the vibration off, the vibrations may be turned on again similar to Step 111.

The automatic operation of the present invention, in addition to controlling the aspiration pump (and perhaps the irrigation pump) as well as the ultrasonic vibration, can also control valves that determine the flow of fluid through the handpiece. In particular, FIG. 6 shows a cross section through one embodiment of a hand piece 14 and FIG. 7 shows an enlarged prospective view of the work tip 15.

The operating end of the work tip may be designed with a cutting knife 224 and multiple fluid channels 250, 250,' which can be segmented into passages A, B, C and D. The three variables can control which channels are used for irrigation and which are used for evacuation (aspiration). For example, if the rate of vacuum rise is too high then one of the aspiration tubes can be converted to an irrigation tube to slow down the vacuum rise.

Figure 6:
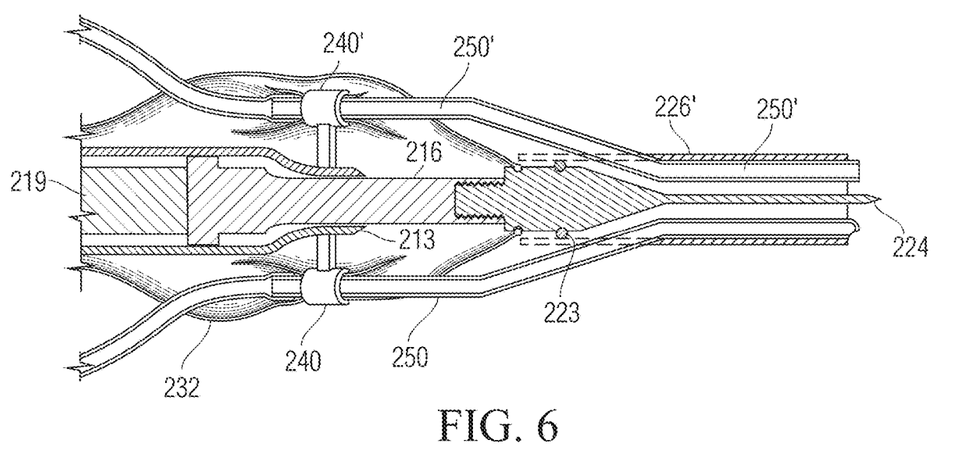
FIG. 6 is an enlarged sectional view of a hand piece that can be utilized with the present invention.

The handpiece shown in FIG. 6 has an ultrasonic transducer 219, which acts through a connecting piece 216 to drive the knife 224 with ultrasonic mechanical vibrations. Irrigation fluid is provided at the surgical site through tube 250' and tissue and fluid are aspirated through tube 250.

Figure 7:
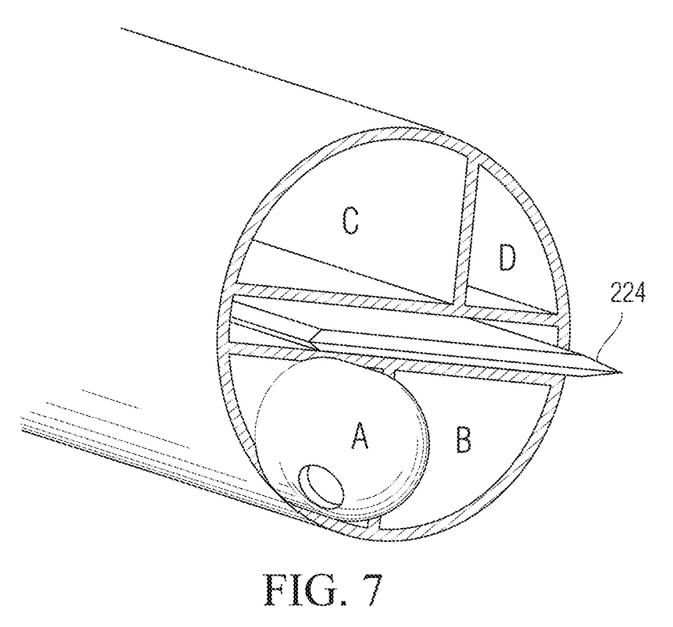
FIG. 7 is a further enlarged view of the distal end of the hand piece showing a work tip that can be utilized with the present invention.
Figure 8:
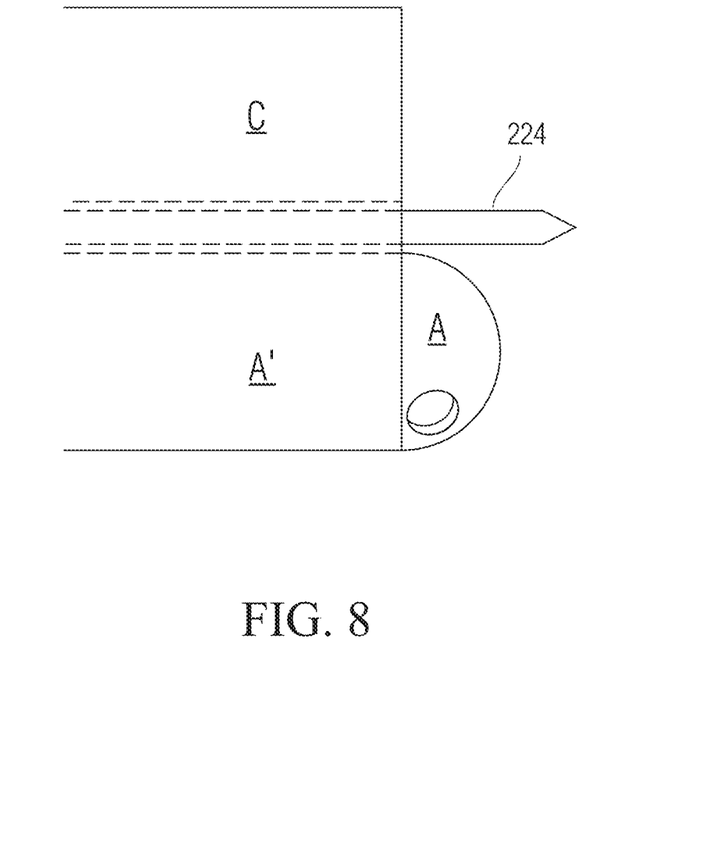
FIG. 8 is an enlarged side view of the work tip.

In FIG. 7 the tube 250' is separated into irrigation passages B and C, while tube 250 is separated into aspiration passages A and D. Valves (not shown) allow the passages to be switched from irrigation to aspiration and vice versa, under the direction of the control system in order to affect the pressure in the aspiration lines. FIG. 8 shows an enlarged side view of the distal end of the work tip. As can be seen the channel A can be shaped at its distal end with a small opening useful in clean up after a phaco operation. Thus, the hand piece can have a dual function, i.e., phacoemulsification and irrigation/aspiration (I/A) cleanup.

The sleeve 226', tubes 250, 250' and the knife 224 along with a sterile sheet 232 can form a single use disposable unit. Also, the sleeve 226' and tubes 250, 250' may be made of a hard plastic such as polysulfone.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A phacoemulsification system comprising:
a hand piece with a cutting tip extending from a distal end thereof, an ultrasonic transducer connected to the cutting tip and mechanically vibrating the cutting tip at an ultrasonic frequency when an ultrasonic electrical signal is applied to the transducer, and an aspiration channel that provides a vacuum force that generates a flow of aspiration fluid that collects fluid and tissue near the distal end of the cutting tip;
a console with an electrical signal generator for generating the ultrasonic electrical signal and providing it to the transducer of the hand piece, at least one source of aspiration force for extracting aspirated fluid and tissue through an aspiration tube from the aspiration channel of the hand piece, at least one irrigation channel for providing irrigation fluid near the distal end of the cutting tip, and a control system for determining the amplitude of the ultrasonic electrical signal and an aspiration flow rate;
a sensor for measuring a pressure in the aspiration channel over a period of time; and
wherein when the sensor detects a change in pressure per unit of time that exceeds a preset limit, the control system causes a first decrease in the amplitude of the ultrasonic electrical signal to a point where there is no longer mechanical vibration of the cutting tip, the first decrease being over a period of time.

2. The phacoemulsification system of claim 1 wherein when the sensor detects a preset pressure limit the control system causes a second decrease in the amplitude of the ultrasonic electrical signal to a point where there is no longer mechanical vibration of the cutting tip, the second decrease being over a period of time and the first and second decreases being independent of each other.

3. The phacoemulsification system of claim 2 wherein the first decrease is linear over a period of time.

4. The phacoemulsification system of claim 2 wherein the second decrease is linear over a period of time.

5. The phacoemulsification system of claim 2 wherein the first decrease is non-linear or curved over a period of time.

6. The phacoemulsification system of claim 2 wherein the second decrease is non-linear or curved over a period of time.

7. The phacoemulsification system of claim 2 wherein the ultrasonic electrical signal is a pulsed signal with a fixed time between pulses and the first decrease occurs a fixed period of time after a pulse.

8. The phacoemulsification system of claim 2 wherein the ultrasonic electrical signal is a pulsed signal with a fixed time between pulses and the second decrease occurs a fixed period of time after a pulse.

9. The phacoemulsification system of claim 2 wherein the ultrasonic electrical signal is a pulsed signal with a variable time between pulses and the first decrease occurs a fixed period of time after a pulse.

10. The phacoemulsification system of claim 2 wherein the ultrasonic electrical signal is a pulsed signal with a variable time between pulses and the second decrease occurs a fixed period of time after a pulse.

11. The phacoemulsification system of claim 2 wherein the ultrasonic electrical signal is a pulsed signal with a variable time between pulses and the first decrease occurs a variable period of time after a pulse.

12. The phacoemulsification system of claim 2 wherein the ultrasonic electrical signal is a pulsed signal with a variable time between pulses and the second decrease occurs after a variable period of time.

13. The phacoemulsification system of claim 2 further including a foot pedal, and wherein the ultrasonic electrical signal is generated to produce ultrasonic vibration of the cutting tip when the foot pedal is activated, and when the foot pedal is not active and the sensor detects a pressure level above the preset pressure limit, the control system turns on the ultrasonic electrical signal to vibrate the cutting tip, even though the foot pedal is not activated.

14. The phacoemulsification system of claim 13 wherein the turning on is linear over a period of time.

15. The phacoemulsification system of claim 13 wherein the turning on is non-linear or curved over a period of time.

16. The phacoemulsification system of claim 13 wherein the ultrasonic electrical signal is a pulsed signal with a fixed time between pulses and the turning on occurs a fixed period of time after a pulse.

17. The phacoemulsification system of claim 13 wherein the ultrasonic electrical signal is a pulsed signal with a variable time between pulses and the turning on occurs a fixed period of time after a pulse.

18. The phacoemulsification system of claim 13 wherein the ultrasonic electrical signal is a pulsed signal with a variable time between pulses and the turning on occurs a variable period of time after a pulse.

19. The phacoemulsification system of claim 2 wherein there is a maximum preset limit for the change in pressure per unit of time, and there is at least one lower preset limit for the change in pressure per unit of time that is lower than the maximum present limit, and wherein when the sensor detects a change in pressure per unit of time that exceeds the lower preset limit, the control system causes a third decrease in the amplitude of the ultrasonic electrical signal that is less than stopping the vibration.

20. The phacoemulsification system of claim 19, wherein when the sensor detects a change in pressure per unit of time that exceeds the lower preset limit, the control system causes a certain decrease in the vacuum force that deceases the flow of aspiration fluid.

21. The phacoemulsification system of claim 20, wherein, when the sensor detects that the pressure is below the first preset pressure limit after the certain decrease in the vacuum force that decreases the flow of the aspiration fluid, the control system causes the flow to subsequently increase.

* * * * *